United States Patent [19]
Schroeppel

[11] Patent Number: 5,413,592
[45] Date of Patent: May 9, 1995

[54] CARDIAC PACEMAKER WITH AUTOMATIC PARAMETER ADJUSTMENT

[75] Inventor: Edward A. Schroeppel, Lake Jackson, Tex.

[73] Assignee: Intermedics, Inc., Angleton, Tex.

[21] Appl. No.: 37,305

[22] Filed: Mar. 26, 1993

[51] Int. Cl.⁶ .......................................... A61N 1/365
[52] U.S. Cl. ..................................................... 607/18
[58] Field of Search ................... 607/17, 18, 19, 21, 607/22, 27, 24, 28, 25, 122

[56] References Cited

U.S. PATENT DOCUMENTS

| | | | |
|---|---|---|---|
| 4,009,721 | 3/1977 | Alcidi | 607/22 |
| 4,365,639 | 12/1982 | Goldreyer | 607/122 |
| 4,644,954 | 2/1987 | Wittkampf et al. | 607/25 |
| 4,708,142 | 11/1987 | De Cote, Jr. | 607/28 |
| 4,733,667 | 3/1988 | Olive et al. | 607/24 |
| 4,905,697 | 3/1990 | Heggs et al. | 607/19 |
| 4,922,930 | 5/1990 | Adkins et al. | 607/19 |
| 4,940,052 | 7/1990 | Mann et al. | 607/19 |
| 5,179,947 | 1/1993 | Meyerson et al. | 607/19 |
| 5,218,961 | 6/1993 | Lekholm | 607/22 |
| 5,330,504 | 7/1994 | Somerville et al. | 607/5 |

Primary Examiner—George Manuel
Attorney, Agent, or Firm—John R. Merkling

[57] ABSTRACT

A cardiac pacemaker which automatically tests for changes in and adjusts output or other parameters in response to detected changes in environmental or physiologic conditions. One or more passive sensors detect environmental or physiologic conditions which may correlate to stimulation thresholds or other parameters. If a change in such conditions is detected, a test or search is initiated to achieve an energy efficient output, to optimize cardiac output, to improve sensing, etc.

48 Claims, 6 Drawing Sheets

CARDIAC PACEMAKER WITH AUTOMATIC PARAMETER ADJUSTMENT

BACKGROUND OF THE INVENTION

1. Field of the Invention

My present invention relates generally to artificial cardiac pacemakers, and more particularly to an implantable cardiac pacemaker which automatically adjusts pulse parameters in response to detected physiologic or environmental conditions.

2. Relevant Background

Early implantable cardiac pacemakers provided only a lower rate limit to prevent life-threatening asystole. Thereafter, more complex pacemakers were designed to respond to sensed electrical conditions in the heart, providing a more physiologic response. For example, if a patient's atrium were producing a relatively normal and physiologically appropriate heart rate, but the signal was not propagating into the ventricle, an appropriate pacemaker might sense atrial beats and pace the ventricle in synchrony. More recently, pacemakers have been proposed which sense environmental or physiologic changes indicative of greater demand, and adjust the allowable minimum heart rate accordingly. An example of an environmental parameter detected by a pacemaker was disclosed by Dahl in U.S. Pat. No. 4,140,132. In that patent, acceleration, which correlates to the activity of the user, was used to adjust the minimum pacing rate. Other so-called rate responsive pacemakers have sensed impedance, pH, $O_2$ and other factors to provide an appropriate physiologic pacing rate.

In addition to the minimum rate, other parameters may be changed to optimize cardiac output. These parameters include refractory periods, stroke volume, sensing amplifier thresholds and stimulating pulse adjustments. To adjust such parameters, pacemakers have been proposed to perform various tests. In other words, the pacemaker produces some signal and detects the heart's response, thereafter adjusting its next signal to the form of the cardiac response. My invention seeks to optimize pacemaker function by initiating such test sequences when sensed physiologic or environmental changes indicate the probability of a change in non-rate parameters.

The magnitude of the output pulse is a non-rate parameter which could be tested and adjusted from time to time when environmental or physiological changes have been sensed. There exists a certain minimum energy necessary to stimulate the muscles of the heart. This energy is delivered by applying a given current or voltage for a particular duration through an electrode. The voltage or current necessary for stimulation is inversely related to the duration of the impulse. This relationship varies from patient to patient and from time to time for the same patient. However, the so-called Lapicque equation describes generally the behavior of the voltage or current with respect to the impulse duration. The equation is:

$$\overline{Y} = \overline{Y}_\infty \left(1 + \frac{T_c}{T}\right)$$

In this equation Y is the pulse amplitude (either voltage or current); $Y_\infty$ is the rheobase or minimum amplitude required to produce a stimulated response as pulse duration goes to infinity; $T_c$ is the chronaxie or minimum duration necessary to achieve stimulation at twice the rheobase; and T is the pulse duration. In the absence of other factors, a pacemaker would last longest if its output pulse expended the minimum energy, a condition which occurs at an impulse duration equal to the geometric mean of the current chronaxie and voltage chronaxie. For further explanation of this phenomenon see, e.g., Bernstein, et al., "Threshold Curve Approximations for Pacemaker Output Programming", *Proceedings of the 2nd European Symposium on Cardiac Pacing*, G. A. Feruglio (ed.), Piccin Medical Books, 1982, pp. 115–120.

In practice, however, the theoretical minimum energy is not used. Because it is critically important that capture be achieved, that is, that the heart be stimulated to contract, a certain safety factor is employed to increase the magnitude of the pulse. Moreover, it is known that the stimulation threshold varies over time after implantation of a new lead. This phenomenon may be associated with the reaction of the body to a foreign body in the heart. Physicians, therefore, compensate for this increased resistance to stimulation.

In addition, researchers have found that the stimulation threshold may change in a given patient in response to increased heart rate, changed physical or emotional stress, or other factors. Various conditions correlated to these factors have, in the past, been sensed in order to vary the pacing rate. These conditions include acceleration, vibration, pH, $O_2$, impedance, and the levels of catecholamines, for example, the level of epinephrine. Such detected changes have not been used, however, to indicate potential variation in the rheobase or other parameters related to the output pulse and to initiate a search for the optimum output level, whereby the energy of the pacemaker can be conserved, and its longevity improved.

Similarly, tests for changes in other parameters such as refractory periods, stroke volume, or amplifier thresholds, have not been conducted in response to sensed changes in physiologic or environmental conditions.

SUMMARY OF MY INVENTION

I have invented a cardiac pacemaker which automatically tests for changes in and adjusts output parameters in response to detected changes in environmental or physiologic conditions. One or more sensors detect environmental or physiologic conditions which may correlate to stimulation thresholds or other parameters. If a change in such conditions is detected, a test or search is initiated to achieve an energy efficient output, to optimize cardiac output, to improve sensing, etc.

With the foregoing in mind, it is the principal object of my invention to provide a cardiac pacemaker which optimizes pacer output by testing for changed parameters in response to sensed changes in environmental or physiologic conditions.

It is also an object of my invention to provide a pacemaker which minimizes energy expenditure and improves pacemaker longevity.

These and other objects of my invention will be apparent from the following detailed description taken with reference to the accompanying drawings.

DETAILED DESCRIPTION OF MY PREFERRED EMBODIMENT

Figure 1:
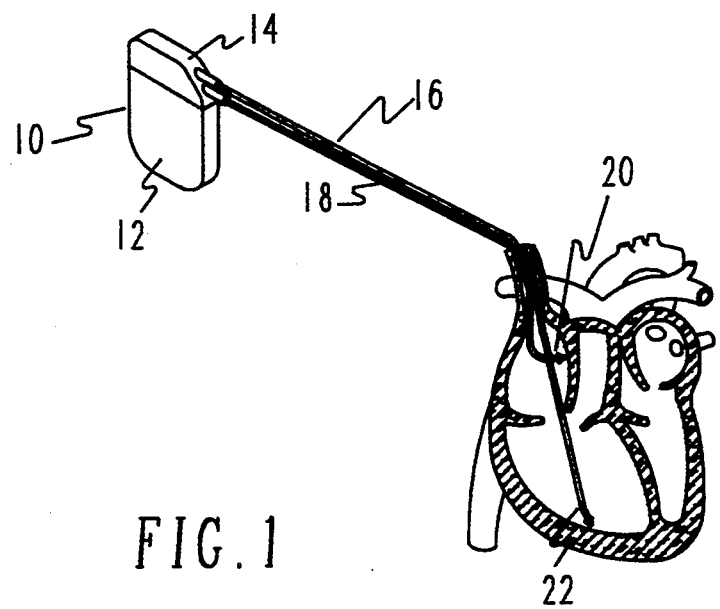
FIG. 1 is a diagram of a pacemaker according to my invention with dual leads connected to a patient's heart.

Referring now to FIG. 1, the cardiac pacemaker 10 of my invention includes a case 12 and header 14. In the illustrated embodiment, a dual chamber pacemaker is described, but a single chamber pacemaker could also use the principles and teachings of my invention. The pacemaker 10 is shown with an atrial lead 16 and a ventricular lead 18. A tip 20 of the atrial lead 16 is implanted near a wall of the right atrium of the heart for sensing and stimulating the atrial chamber. Similarly, a tip 22 of the ventricular lead 18 is implanted in the right ventricle of the heart for sensing and stimulating the ventricle.

Figure 2:
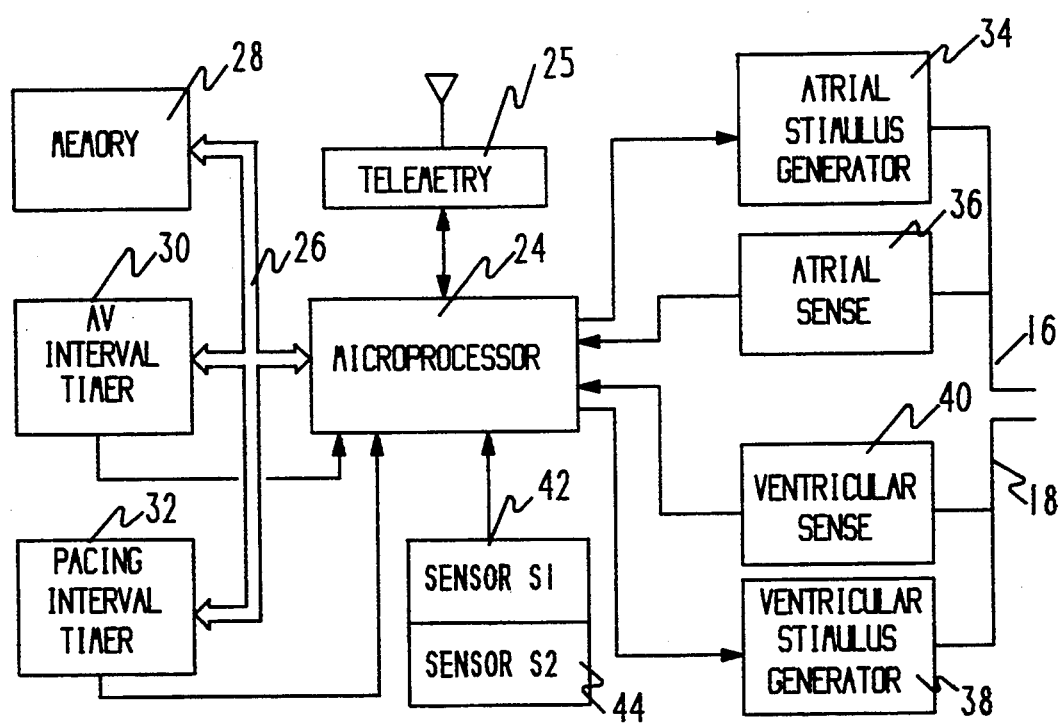
FIG. 2 is a block diagram of the pacemaker of my invention.

With reference to FIG. 2, the pacemaker 10 comprises a microprocessor 24 which controls the basic functions of the pacemaker. Telemetry circuits 25 permit communication between the pacemaker and a programmer (not shown) external to the patient's body. The microprocessor is connected through a bus 26 to additional memory 28 for storing programs or data in connection with the operation of the pacemaker. The microprocessor is also provided with various clocks, such as AV interval timer 30 or pacing interval timer 32. In the disclosed embodiment, the pacemaker 10 stimulates the heart in both the atrium and the ventricle. It has an atrial stimulus generator 34 which is controlled by the microprocessor 24. Both the duration and amplitude of the output pulse are controlled by the microprocessor. The output pulse is delivered to the heart along the atrial lead 16. Similarly, an atrial sense circuit 36 is connected to the lead 16. It provides information to the microprocessor on the electrical condition of the atrium.

A ventricular stimulus generator 38 stimulates the ventricle through the ventricular lead 18. This generator 38, like the atrial stimulus generator 34, is controlled by the microprocessor 24. The duration and amplitude of the ventricular stimulus can be controlled, as well as its timing. A ventricular sense circuit 40 detects the electrical condition of the ventricle through the ventricular lead and communicates that information to the microprocessor 24.

In addition to the information on the electrical condition of the heart, received through the atrial and ventricular sense circuits, the microprocessor receives information from one or more sensors such as sensor S1 42 and sensor S2 44. For my preferred embodiment, I have illustrated two sensors, whose output may be used to control both the rate of cardiac stimulation, as is known in the art, and to initiate automatic output adjustment. However, my invention may be used with pacers which employ one or multiple sensors or simply rely on the information gathered on the atrial and ventricular sense circuits to indicate changing environmental or physiologic conditions.

In my preferred embodiment, sensor S1 42 responds rapidly to exercise. The sensor might be an accelerometer, as disclosed by Dahl, U.S. Pat. No. 4,140,132, or a vibration sensor, as disclosed by Anderson, U.S. Pat. No. 4,428,378. Sensor S2 44 responds more slowly to changing conditions, but in a more physiologic manner. A temperature sensor, for example, sensing central venous temperature, or an oxygen saturation sensor, may be used. Note that the sensors may be either in the case 12 of the pacemaker or external to the case. If external to the case they may be located on one or more of the leads 16, 18. For example, accelerometer or vibration sensors are typically located within the case of the pacemaker, while temperature or oxygen sensors are typically located on the leads. Other parameters known in the art which may be sensed included pH, impedance, or catecholamine levels.

Figure 3:
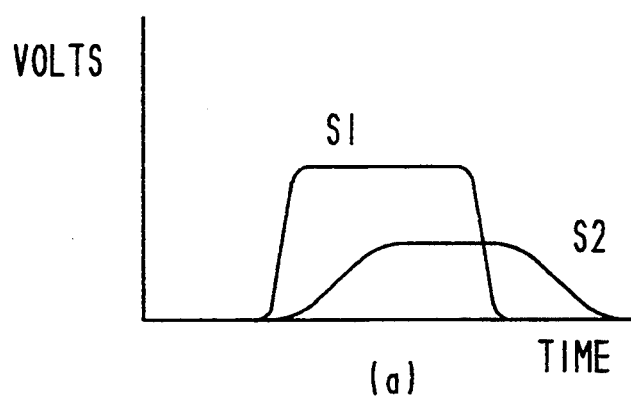
FIG. 3 are graphs of detected parameters.
Figure 3:
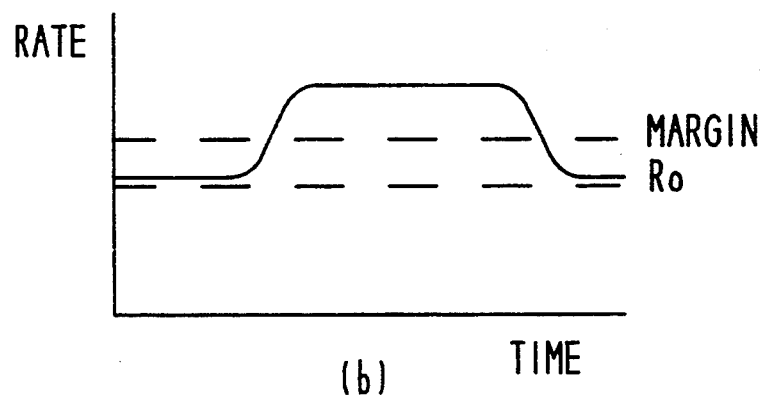
Figure 3:
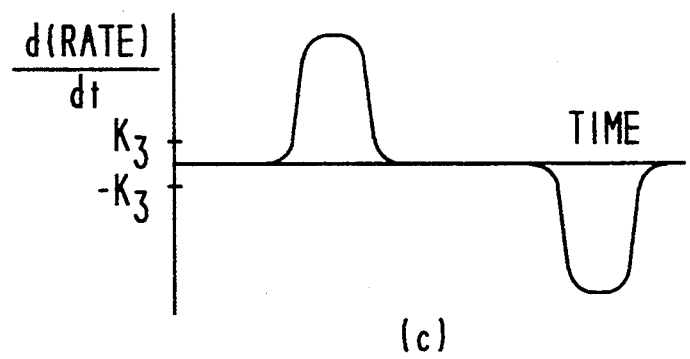

My preferred embodiment includes a rate-responsive aspect, as described, for example, by Alt in U.S. Pat. No. 4,926,863. The basic function of such a pacemaker can be described with reference to FIG. 3. In FIG. 3, graph (a), the voltage outputs of the sensors S1 and S2 are graphed with respect to time. In response to increased exercise or activity, the voltage of S1 can be expected to rise relatively quickly. The voltage of S2, on the other hand, rises more slowly but continues at an elevated level after activity has stopped, producing a "cool down" period. In response, the pacemaker invokes an algorithm, a type of which will be described below, to increase the base rate of the pacemaker as shown in graph (b) of FIG. 3. If the activity is sufficiently intense, the rate will change beyond a base rate $R_0$ plus some selected margin. If this margin is exceeded, my invention should be invoked to search for an appropriate threshold. In addition, it will be apparent that the rate of change of the rate with respect to time will vary as shown in graph (c) of FIG. 3. Thus, a positive impulse or spike in the time derivative of the rate would be expected as the rate rises in response to increased exercise and a negative impulse would be expected when the rate again falls to its base rate. Either change can indicate changed parameters for which a search or test is appropriate. In my preferred embodiment, these parameters are used to initiate a search for optimum output level, as i will now explain in connection with FIG. 4. Note that my invention may be implemented without a change in the pacing rate. What is required is an essentially passive sensor means which detects changing physiologic or environmental conditions.

Figure 4:
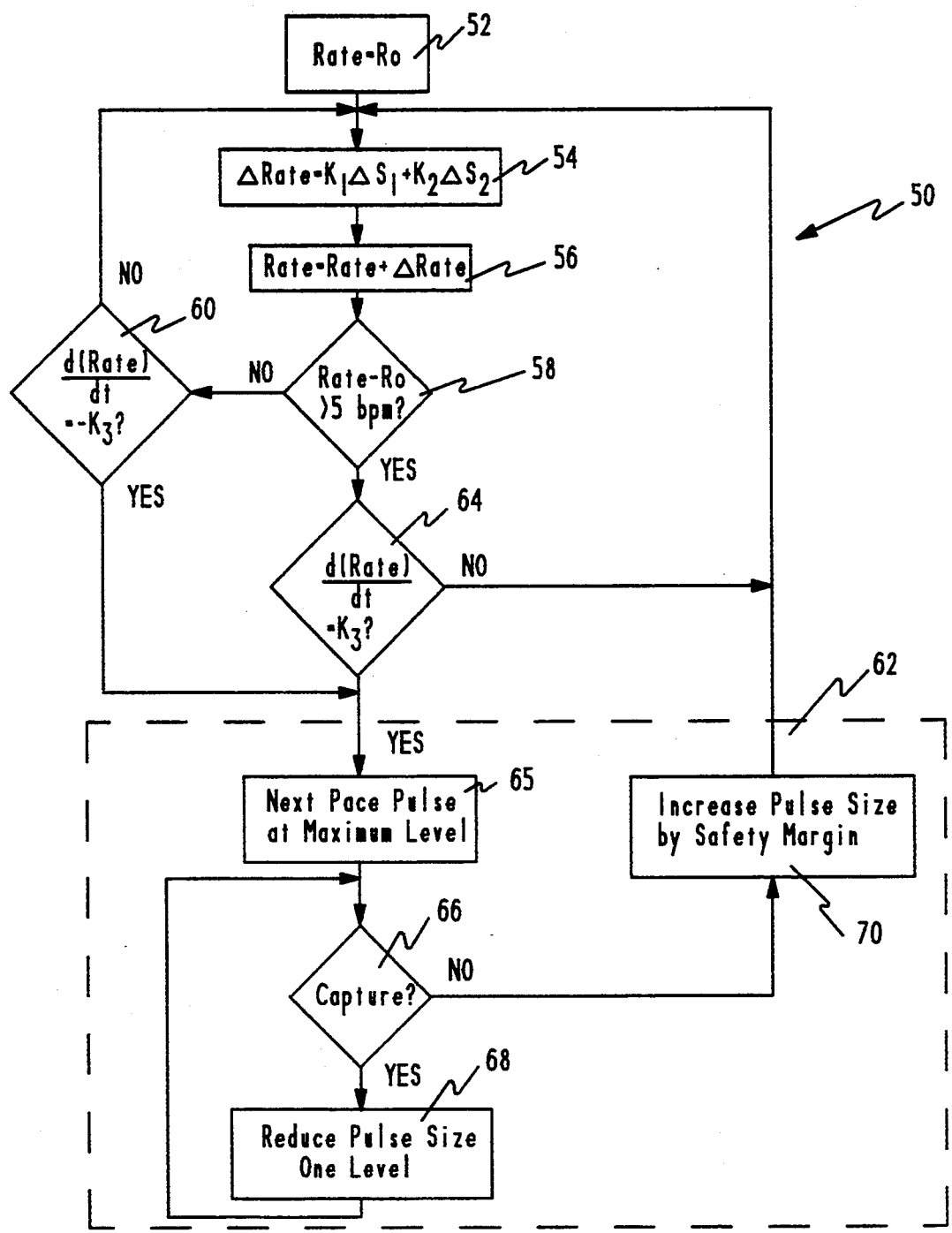
FIG. 4 is a flow chart of an algorithm with pulse level adjustment.

FIG. 4 illustrates an algorithm 50 for implementing my invention. In a rate responsive pacemaker the rate of pacing is initially set 52 to a base rate $R_0$. In response to changes in the voltage of the sensors, a change of rate will be generated 54. In step 54, $\Delta S_1$ represents a change in voltage from sensor S1, $\Delta S_2$ represents the change in voltage from sensor S2 and $K_1$ and $K_2$ are constants chosen to reflect the nature of the selected sensors. The new rate is then set 56 equal to the old rate plus the change of rate. The microprocessor 24 then tests 58 the rate to see if it has changed significantly from the base rate $R_0$. In the illustrated example, rate minus $R_0$ must be greater than 5 beats a minute. If it is not, the rate of change of the rate with respect to time is checked 60 to see if it is negative, in other words, to see if the rate is returning towards its initial setting or not. A constant $-K_3$ is selected near but not equal to 0. This constant actually would be implemented as a range since the change of rate is not continuously monitored by the algorithm. Falling within the range represented by $-K_3$ indicates that the change of rate is approaching the initial setting and also that the rate of change is sufficiently stable so that it may be inferred that change in exercise is over. (Note that steady exercise represents a stable condition just as rest does.) If a stable condition does not exist, the algorithm returns to step 54. If the stability condition is met, the microprocessor implements a threshold search 62. On the other hand, if the rate is detected as elevated in step 58, the stability of the rate of the change of rate is detected in a comparison step 64 with a positive constant range K3 in the same manner as in step 60. If the rate is not sufficiently stable, the control is returned to step 54. If the stability of the criterion is met, control is shifted to the threshold search algorithm 62.

In the threshold search algorithm 62, the pulse is set initially to the maximum level 65. Through the atrial and ventricular sense circuits 36, 40, the microprocessor 24 determines whether capture 66 has been achieved. If capture is detected, the pulse size is reduced 68 on the next cycle, and this process continues until capture is lost. Once capture is lost, the pulse size is increased 70 by a preset safety margin and the microprocessor returns to other functions. Broadly, the threshold search algorithm is an active test, wherein the pacemaker generates a signal and detects the heart's response. In contrast, the rate algorithm represents an essentially passive sensing or a physiologic or environmental condition.

Figure 5:
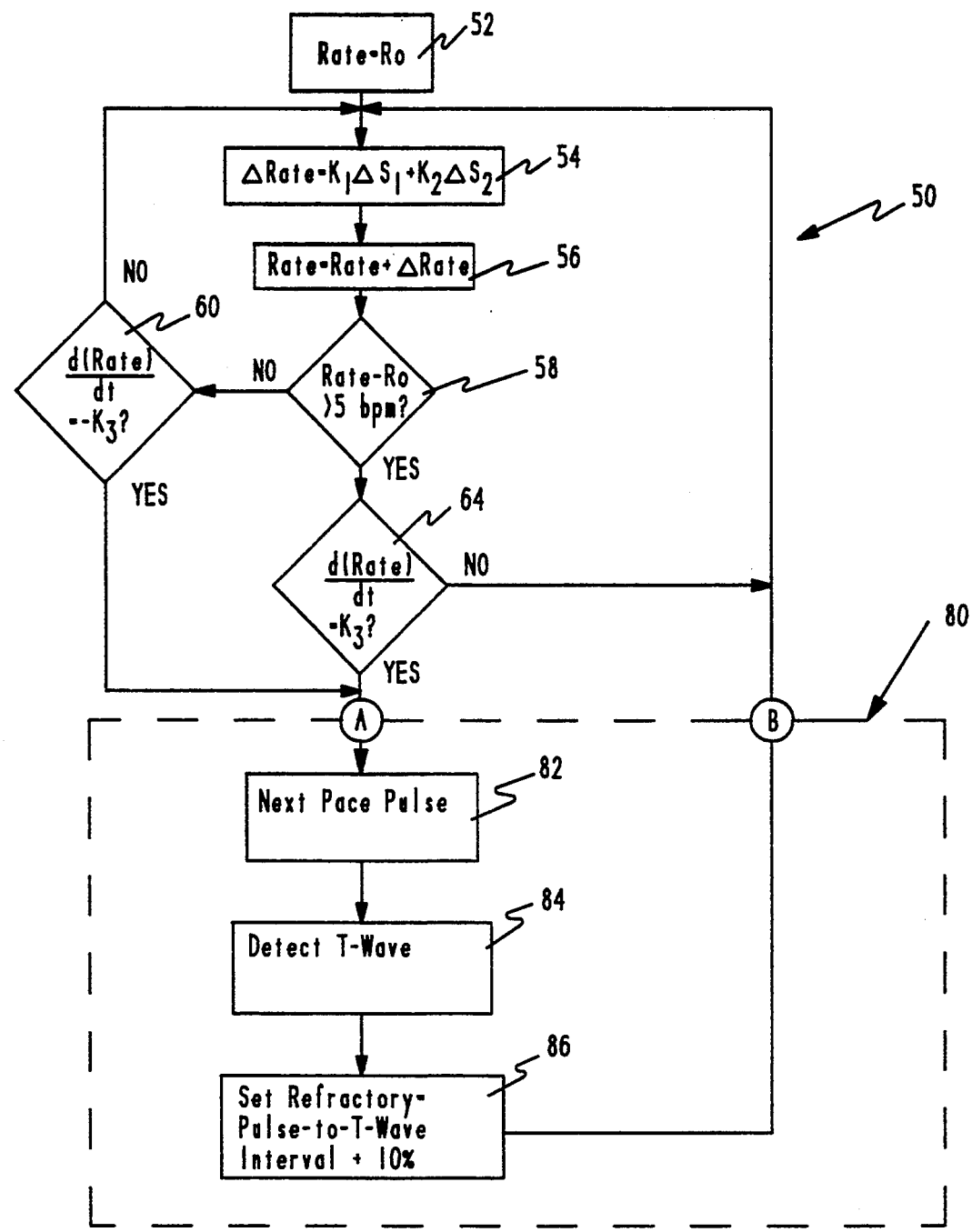
FIG. 5 is a flow chart of an algorithm with refractory period adjustment.
Figure 6:
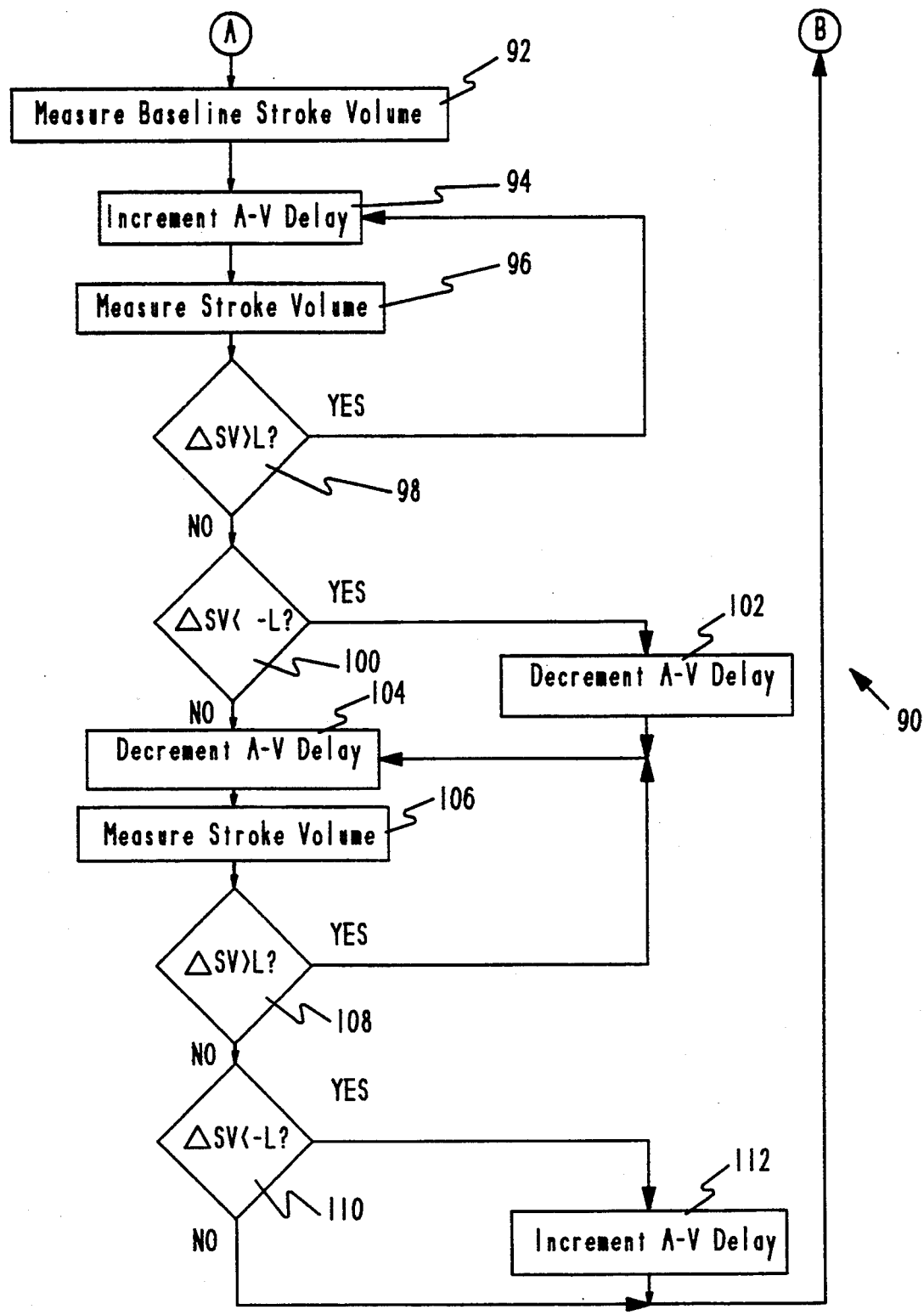
FIG. 6 is a flow chart of an algorithm with stroke volume adjustment.
Figure 7:
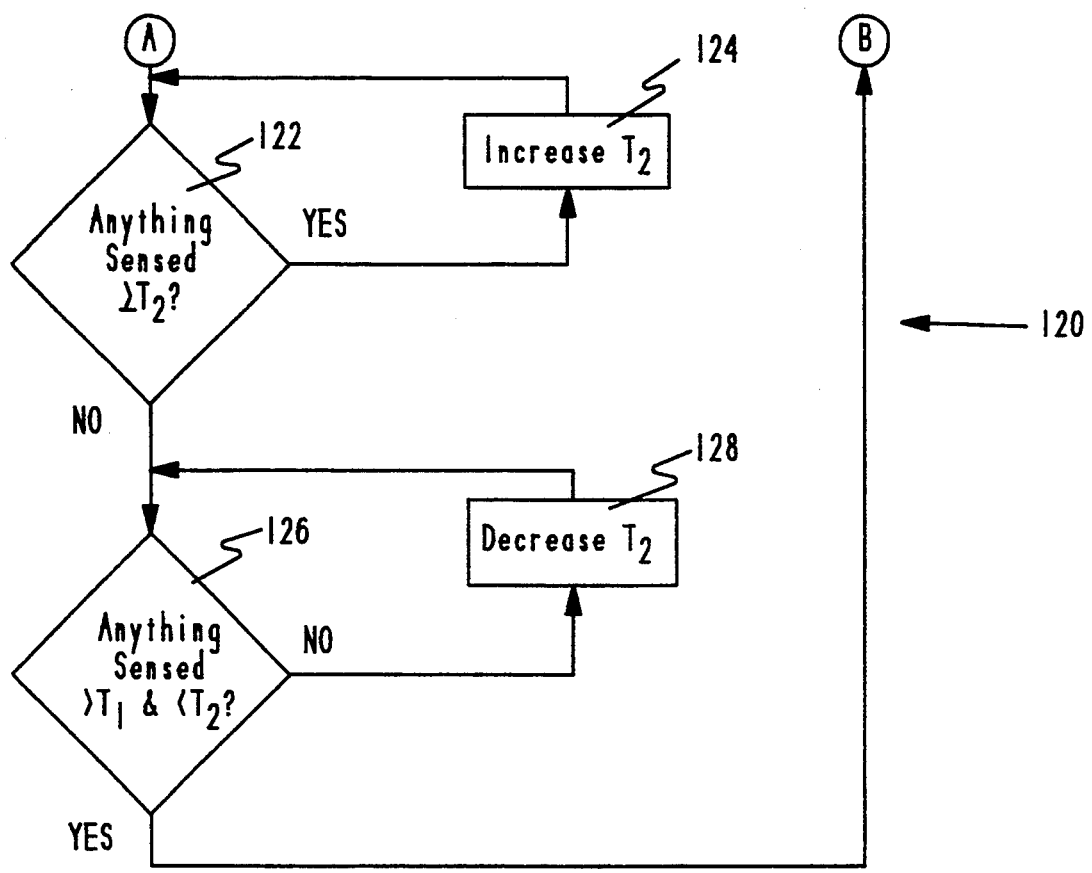
FIG. 7 is a flow chart of an algorithm with threshold (amplifier) adjustment.

FIGS. 5, 6 and 7 illustrate additional parameters which may be adjusted in response to a detected change in condition. In connection with each of the examples shown in these figures, there would be a change detecting section similar to the rate control described in connection with FIG. 4 above. This is illustrated in the upper portion of FIG. 5 to the connection letters A and B. These points are common to each of the examples herein. For simplicity, therefore, they are shown merely as points A and B, respectively, in each of FIGS. 6 and 7.

FIG. 5 illustrates adjustment of ventricular refractory control, a parameter which may change in response to changing physiological conditions. Consequently, change of rate is indicative of a potential need to adjust this parameter. If a change in conditions is sensed, a search or test may be initiated to optimize the ventricular refractory period, as shown in FIG. 5. If a change has occurred, program control would pass through the point A into a parameter adjustment routine 80. When a pacer produces its next pacing pulse 82, it would begin timing an interval, while sensing for the evoked T-wave produced by the contraction of the heart. When the T-wave is detected 84, the timer is checked so that the interval is now known. Upon sensing the T-wave, the pacemaker then resets its internal refractory period to a length equal to the measured time plus some safety margin 86. For example, the safety margin may be an additional 10% of the measured interval. Program control is then returned to the balance of the program through control point B.

FIG. 6 illustrates an embodiment of my invention for optimizing cardiac output. In this example, an optimum A-V delay in a dual chamber pacemaker is sought. I discuss a baseline stroke volume, although other parameters are also appropriate. Stroke volume and other such cardiac output related parameters are usually relatively difficult to measure or may consume a relatively large amount of pacemaker current in measurement. Consequently, it is preferred that such measurements be performed infrequently. By initiating a measurement only when other changes have indicated that a change in the stroke volume or other cardiac output parameter may have occurred, the efficiency of the measurement can be increased. Referring now to FIG. 6, as in the previous examples discussed in connection with FIGS. 4 and 5, when the change indicative of an altered physiologic state has been detected, program control proceeds to the entry point A into an optimization routine 90. The pacemaker then measures the baseline stroke volume at step 92. In a subsequent cardiac cycle the A-V delay is incremented 94 and this stroke volume is again measured 96. If the difference between these two measurements is greater than some predetermined margin L at step 98, the program control is returned to step 94 and the A-V delay is again incremented. This cycle continues until no improvement or no further improvement in stroke volume is seen, at which point the program tests 100 to see if the difference between the baseline stroke volume is less than some preselected margin $-L$. If a significant decrease in stroke volume has been detected at 100, the A-V delay is decremented first at step 102 and then a second time at step 104. If no significant change has taken place, the A-V delay is decremented only once at step 104. The stroke volume is then measured again at 106 and the program tests 108 to see if the stroke volume has improved, again by the margin of L. If the stroke volume has improved, the program once again decrements the A-V delay at 104 and the cycle is repeated until there is no improvement or no further improvement in the stroke volume. The program then tests once again for significant decrease in stroke volume at 110. If there is a significant decrease, the A-V delay is incremented at 112 one time and program control is returned to the balance of the program through control point B. If there is no significant change detected at step 110, the program control is returned directly to control point B.

It is known in the art of pacemakers for pacemakers to continuously monitor and change such parameters as refractory periods and amplifier sensitivity. An example of such a pacemaker is disclosed in U.S. Pat. No. 4,766,902. It is possible, however, to adjust such parameters only when there is a detected likelihood that a change has occurred. If a stable period following a change in rate has been achieved as described above in connection with FIGS. 4 and 5, microprocessor control may again be passed to a control point A into a sensitivity routine 120 illustrated in FIG. 7. The algorithm illustrated in FIG. 7 assumes the existence of two thresholds T1 and T2, with T2 greater than T1. These thresholds may be voltages associated with the sensitivity of the amplifiers in the pacemaker. Furthermore, T1 is different from T2 by a preselected margin. Any change in T2, therefore, will be accompanied by a corresponding change in T1. After program control passes through point A in FIG. 7, the microprocessor tests if a selected phenomenon was detected greater than or equal to threshold T2 at step 122. If anything is sensed (for example, a voltage larger in magnitude than threshold T2) T2 should be increased 124. This is associated with a corresponding increase in T1 and effectively decreases the sensitivity of the input amplifiers. If nothing is sensed above threshold T2, the microprocessor tests at 126 to see if any phenomenon is sensed between T1 and T2. If nothing is sensed, the sensitivity of the amplifiers is too low, and T2 must be decreased 128, with a corresponding decrease in T1. If there is a phenomenon sensed between the two thresholds, the sensitivity is correctly set and microprocessor control should be returned through central point B in FIG. 7.

The foregoing examples are offered as illustrative of the types of parameters that may be changed in response to a detected change in condition. A detected change in condition may not result in an actual change in a parameter; rather, the search algorithm for the selected parameter is initiated at a favorable time. The various parameters may be used together or separately or in any combination, which selection is deemed to be within the capability of one skilled in the art. Moreover, the pacemaker algorithm may be biased in favor of a particular sensor or output for the detection of a portion of the algorithm and with corresponding association to the parameter search algorithms. That is, where one or more sensor inputs are used, as described above, some response from a particular subset of these sensors may appropriately initiate optimization of certain parameters, but not others. For example, if sensor S1 is an activity sensor and sensor S2 is a stroke volume sensor, then a change in stroke volume alone may be sufficient to initiate a search for a change in A-V delay. As a further example, a third sensor may be a Q-T sensor. The particular output from this sensor, standing alone, may be sufficient to initiate a search for a change in the ventricular refractory period.

While I have described my preferred embodiment of the invention, it will be apparent to those skilled in the art that various modifications may be implemented without departing from the principles of my invention. Accordingly, it is intended that the invention be limited only by the appended claims.

I claim as my invention:

1. A cardiac pacemaker comprising
a pulse generator for producing heart-stimulating pulses,
means for electrically connecting said pulse generator to a human heart,
at least one sensor for sensing a first variable parameter indicative of physiologic change,
means responsive to changes in said first parameter indicative of physiologic change for initiating testing of a second variable parameter, and
testing means responsive to said means for initiating testing, said testing means comprising
means for stimulating the heart,
means for detecting capture, and
means for varying the magnitude of a stimulating pulse.

2. The cardiac pacemaker according to claim 1 wherein said at least one sensor comprises a sensor for detecting environmental changes.

3. The cardiac pacemaker according to claim 2 wherein said sensor for detecting environmental changes is an accelerometer.

4. The cardiac pacemaker according to claim 2 wherein said sensor for detecting environmental changes is a vibration sensor.

5. The cardiac pacemaker according to claim 1 wherein said at least one sensor comprises a physiologic condition sensor.

6. The cardiac pacemaker according to claim 5 wherein said physiologic condition sensor comprises a temperature sensor.

7. The cardiac pacemaker according to claim 5 wherein said physiologic condition sensor comprises a pH sensor.

8. The cardiac pacemaker according to claim 5 wherein said physiologic condition sensor comprises an oxygen sensor.

9. The cardiac pacemaker according to claim 5 wherein said physiologic condition sensor comprises an impedance sensor.

10. The cardiac pacemaker according to claim 5 wherein said physiologic condition sensor comprises a catecholamine sensor.

11. The cardiac pacemaker according to claim 1 wherein said at least one sensor comprises a plurality of sensors.

12. The cardiac pacemaker according to claim 11 wherein said plurality of sensors comprise an accelerometer and a temperature sensor.

13. A cardiac pacemaker comprising
a pulse generator for producing heart-stimulating pulses,
means for electrically connecting said pulse generator to a human heart,
at least one sensor for sensing a first variable parameter indicative of physiologic change,
means responsive to changes in said first parameter indicative of physiologic change for initiating testing of a second variable parameter, and
testing means responsive to said means for initiating testing, said testing means comprising
means for stimulating the heart,
means for detecting a T-wave, and
means for altering the duration of a refractory period.

14. The cardiac pacemaker according to claim 13 wherein said at least one sensor comprises a sensor for detecting environmental changes.

15. The cardiac pacemaker according to claim 14 wherein said sensor for detecting environmental changes is an accelerometer.

16. The cardiac pacemaker according to claim 14 wherein said sensor for detecting environmental changes is a vibration sensor.

17. The cardiac pacemaker according to claim 13 wherein said at least one sensor comprises a physiologic condition sensor.

18. The cardiac pacemaker according to claim 17 wherein said physiologic condition sensor comprises a temperature sensor.

19. The cardiac pacemaker according to claim 17 wherein said physiologic condition sensor comprises a pH sensor.

20. The cardiac pacemaker according to claim 17 wherein said physiologic condition sensor comprises an oxygen sensor.

21. The cardiac pacemaker according to claim 17 wherein said physiologic condition sensor comprises an impedance sensor.

22. The cardiac pacemaker according to claim 17 wherein said physiologic condition sensor comprises a catecholamine sensor.

23. The cardiac pacemaker according to claim 13 wherein said at least one sensor comprises a plurality of sensors.

24. The cardiac pacemaker according to claim 23 wherein said plurality of sensors comprise an accelerometer and a temperature sensor.

25. A cardiac pacemaker comprising a pulse generator for producing heart-stimulating pulses, means for electrically connecting said pulse generator to a human heart, at least one sensor for sensing a first variable parameter indicative of physiologic change, means responsive to changes in said first parameter indicative of physiologic change for initiating testing of a second variable parameter, and testing means responsive to said means for initiating testing, said testing means comprising means for measuring the stroke volume, and means for varying magnitude of an A-V delay of a stimulating pulse.

26. The cardiac pacemaker according to claim 25 wherein said at least one sensor comprises a sensor for detecting environmental changes.

27. The cardiac pacemaker according to claim 26 wherein said sensor for detecting environmental changes is an accelerometer.

28. The cardiac pacemaker according to claim 26 wherein said sensor for detecting environmental changes is a vibration sensor.

29. The cardiac pacemaker according to claim 25 wherein said at least one sensor comprises a physiologic condition sensor.

30. The cardiac pacemaker according to claim 29 wherein said physiologic condition sensor comprises a temperature sensor.

31. The cardiac pacemaker according to claim 29 wherein said physiologic condition sensor comprises a pH sensor.

32. The cardiac pacemaker according to claim 29 wherein said physiologic condition sensor comprises an oxygen sensor.

33. The cardiac pacemaker according to claim 29 wherein said physiologic condition sensor comprises an impedance sensor.

34. The cardiac pacemaker according to claim 29 wherein said physiologic condition sensor comprises a catecholamine sensor.

35. The cardiac pacemaker according to claim 25 wherein said at least one sensor comprises a plurality of sensors.

36. The cardiac pacemaker according to claim 35 wherein said plurality of sensors comprise an accelerometer and a temperature sensor.

37. A cardiac pacemaker comprising a pulse generator for producing heart-stimulating pulses, means for electrically connecting said pulse generator to a human heart, at least one sensor for sensing a first variable parameter indicative of physiologic change, means responsive to changes in said first parameter indicative of physiologic change for initiating testing of a second variable parameter, and testing means responsive to said means for initiating testing, said testing means comprising means for detecting intrinsic cardiac signals, and means for altering amplification gain.

38. The cardiac pacemaker according to claim 37 wherein said at least one sensor comprises a sensor for detecting environmental changes.

39. The cardiac pacemaker according to claim 38 wherein said sensor for detecting environmental changes is an accelerometer.

40. The cardiac pacemaker according to claim 38 wherein said sensor for detecting environmental changes is a vibration sensor.

41. The cardiac pacemaker according to claim 37 wherein said at least one sensor comprises a physiologic condition sensor.

42. The cardiac pacemaker according to claim 41 wherein said physiologic condition sensor comprises a temperature sensor.

43. The cardiac pacemaker according to claim 41 wherein said physiologic condition sensor comprises a pH sensor.

44. The cardiac pacemaker according to claim 41 wherein said physiologic condition sensor comprises an oxygen sensor.

45. The cardiac pacemaker according to claim 41 wherein said physiologic condition sensor comprises an impedance sensor.

46. The cardiac pacemaker according to claim 41 wherein said physiologic condition sensor comprises a catecholamine sensor.

47. The cardiac pacemaker according to claim 37 wherein said at least one sensor comprises a plurality of sensors.

48. The cardiac pacemaker according to claim 47 wherein said plurality of sensors comprise an accelerometer and a temperature sensor,

* * * * *